United States Patent [19]
Loewy et al.

[11] Patent Number: 5,939,291
[45] Date of Patent: *Aug. 17, 1999

[54] MICROFLUIDIC METHOD FOR NUCLEIC ACID AMPLIFICATION

[75] Inventors: Zvi Loewy, Fair Lawn; Rajan Kumar, Plainsboro, both of N.J.

[73] Assignee: Sarnoff Corporation, Princeton, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/665,209

[22] Filed: Jun. 14, 1996

[51] Int. Cl.$^6$ .............................. C12P 19/34; C12Q 1/68
[52] U.S. Cl. ................................. 435/91.2; 435/6
[58] Field of Search .................. 435/5, 6, 91.2; 425/288; 536/24.3, 24.33

[56] References Cited

U.S. PATENT DOCUMENTS

| | | | |
|---|---|---|---|
| 5,229,227 | 7/1993 | Webber | 436/94 |
| 5,494,810 | 2/1996 | Barany et al. | 435/91.52 |
| 5,527,670 | 6/1996 | Stanley | 435/6 |
| 5,545,540 | 8/1996 | Mian | 435/91.2 |
| 5,578,460 | 11/1996 | Ebersole et al. | 435/29 |
| 5,707,026 | 1/1998 | Denoya et al. | 435/119 |
| 5,726,026 | 3/1998 | Wilding et al. | 435/7.21 |
| B1 4,683,202 | 11/1990 | Mullis | 435/91 |

FOREIGN PATENT DOCUMENTS 0 320 308  6/1989  European Pat. Off. .

OTHER PUBLICATIONS

Copy of International Search Report dated Sep. 3, 1997 from corresponding international application.
Schachter et al., *J. Clin. Microbial.*, 32:2540–2543 (1994).
Walker et al., *PCR Methods And Applications*, 3:1–6 (1993).
van Gemen et al., *J. Virol. Methods*, 43:177–188 (1993).
Pfyffer et al., *J. Clin. Micro.*, 34:834–841 (1996).
Rubin et al., *Nucleic Acids Res.*, 23:3547–3553 (1995).
Ng and Orgel, *Nucleic Acids Res.*, 15:3573–3580 (1987).
Kuhn et al., *Cold Spring Harbor Symposia on Quantitative Biology*, 43;63–67 (1978).
Radding, *Ann. Rev. Genetics*, 16:405–437 (1982).
*Biomagnetic Techniques In Molecular Biology*, (published by Dynal Corporation, pp. 9–27.
Ausubel et al., Short Protocols In Molecular Biology, John Wiley & Sons, Unit 6.4, pp. 6–7 to 6–10, and Units 4.6–4.7, pp. 4–14 to 4–20, 1992.
Maniatis et al. Transfer of DNA from agarose gels to nitrocelluilose paper Mocelular cloning a laboratory manual, p. 383.

*Primary Examiner*—Eggerton A. Campbell
*Attorney, Agent, or Firm*—William J. Burke

[57] ABSTRACT

The nucleic acid amplification reactions of the present invention are conducted isothermally, using non-thermal denaturation procedures, such as occurs in chemical- or electrostatic-based denaturation. Embodiments are set forth for automated forms of the claimed procedures.

20 Claims, No Drawings

MICROFLUIDIC METHOD FOR NUCLEIC ACID AMPLIFICATION

This invention was made with U.S. Government support under Contract No. 70NANB5H1037. The U.S. Government has certain rights in this invention.

This patent application is being concurrently filed with the following related U.S. patent applications: METHOD FOR POLYNUCLEOTIDE SEQUENCING, R. Kumar and P. Heaney, inventors, Ser. No. 08/665,210; NUCLEASE PROTECTION ASSAYS, R. Kumar, inventor, Ser. No. 08/665,104; METHOD FOR AMPLIFYING A POLYNUCLEOTIDE, Z. Loewy, inventor, Ser. No. 08/663,688; AUTOMATED NUCLEIC ACID PREPARATION, D. Southgate and Z. Loewy, inventors, Ser. No. 08/664,780; PADLOCK PROBE DETECTION, R. Kumar, inventor, Ser. No. 08/665,208. This patent application is related to the following copending U.S. patent applications: Ser. No. 60/009,517, filed Nov. 3, 1995, Attorney Docket No. DSRC/11772; Ser. No. 60/006,202, filed Nov. 3, 1995, Attorney Docket No. DSRC/11904; and Ser. No. 60/010,513, filed Jan. 24, 1996.

The present invention relates to the field of polynucleotide analysis, and, in particular, to a method and a device for automating this method, for conducting isothermal nucleic acid amplification reactions.

Amplification of a specific segment of nucleic acid is an important component not only for the conduct of genetic research, but increasingly for the conduct of medical diagnostics, including the determination of either inborn errors of metabolism and other disorders caused by one's genetic make-up, or pathogens, such as viruses that cause AIDS and hepatitis, among others, and bacteria that cause pneumonia and diphtheria, among others. Moreover, nucleic acid amplification methods are also increasingly important for forensic evidence, wherein, for example, a perpetrator can be connected to his or her crime by correlating specific segments of nucleic acid found in samples of tissue or other biological samples (such as blood, semen, tissue scraped from a victim's fingernails, and the like) isolated from the crime scene or the victim with corresponding such segments found in the genetic make-up of a suspect.

The standard methods of nucleic acid amplification typically entail the repeated step of denaturing the amplification products in order to conduct an ensuing round of amplification. For example, in the typical polymerase chain reaction ("PCR"), a target DNA is first denatured, usually by heat at 90° C. to 100° C., and allowed to renature in the presence of two different primers that span a region of the target nucleic acid at about 30° C. to 50° C., and which respectively are specific for the two separated strands of the DNA. A DNA polymerase derived from thermophilic bacteria is included in a reaction mixture to extend the primers; the polymerase reaction ensues at between about 50° C. and 75° C., after which the PCR reactants are subjected to repeated cycles of denaturation (90° C. to 100° C.) followed by renaturation (30° C. to 50° C.) and extension (50° C. and 75° C.) until a prescribed level of amplification has occurred. The conventional PCR method requires use of a thermal cycler for causing the sequential denaturations and renaturations of the nucleic acid and the amplification products (i.e., amplicons) of the amplification reaction, which can be effected manually or by an instrument. Either way, a technician is required to set up the amplification reaction, thereby incurring a substantial risk of human error in this analysis. Of course, chemical means are available for denaturing duplex nucleic acids, however a cyclic amplification process demarked by base-denaturation, for example, followed by neutralization and replenishment of reaction mix for a succeeding round of amplification will result in vastly diluted reaction products.

Concerns regarding accuracy, including the increased potential for human error in non-automated procedures, cost of capital equipment required for thermal-based automated procedures, and the inherent difficulties posed by the chemical means alternative to thermal-based denaturation have operated to prevent the more widespread use of amplification procedures in medical diagnostics and forensics.

Accordingly, there is a need for an automatable method for nucleic acid amplification. Further, there is a need for a device that employs the automatable method for nucleic acid amplification. The present invention answers these needs, as set forth hereinbelow.

SUMMARY OF THE INVENTION

The present method provides a solution to the problem of doing nucleic acid amplification isothermally such that the process can be automated. No thermal cyclers are required necessarily. Compared to heat denaturation, chemical or electrostatic denaturation as disclosed herein is more efficient in that more of the molecules in a sample denature in response to the addition of base, or subjection to an electric field in the case of electrostatic denaturation, and do so virtually instantaneously and irreversibly, at least, respectively, until the base is neutralized or the electric field terminated. Moreover, using the microfluidic environment set forth in copending application Ser. No. 60/010,513, in combination with microparticles capable of specifically binding to nucleic acids and being locked in place in the microfluidics device, the inherent volume expanding aspect of chemical denaturation is overcome. Moreover, the chemical denaturation in combination with an electrostatic denaturation for amplicons is believed to result in yet higher efficiencies.

These efficiencies are made possible by the use of the microfluidic environment, which is preferably housed in a cassette. In the cassette are various fluid chambers that are interconnected serially, and at points multiply, which provide the reagents, reaction chamber, and waste receptacle. Because the nucleic acid, both the target and amplicon varieties, can be held in place by microparticles having specific affinity for nucleic acid, and having paramagnetic characteristics allowing the device to hold the nucleic acid complexed microparticles in place at the reaction chamber, for example, while the incubating fluids containing alternatively a reaction mix, NaOH denaturant, HCl neutralizer, and reaction mix again, for example, pass through and occupy the reaction chamber for predetermined times, ever-increasing numbers of amplicons are generated and become attached to the microparticles.

In its essence, then, the present invention relates to a nucleic acid amplification device comprising a reaction chamber, wherein the device uses non-thermal means for denaturing nucleic acid in the reaction chamber. The reaction chamber preferably remains at a constant temperature within about two degrees centigrade, which is preferably between about 20° C. and 75° C.

In greater particularity, the inventive device incorporates a non-thermal means of denaturation comprising:
(A) using chemical denaturation, comprising:
   (ii) contacting the nucleic acid with a base; or
(B) using electrostatic denaturation, comprising:
   (i) providing primers that are respectively complementary to the W and C strands of the nucleic acid, and have attached thereto electrostatic microparticles of positive or negative charge, wherein the primers complementary to the W strand all have the same charge and the primers complementary to the C strand all have the opposite charge;

(ii) denaturing the nucleic acid a first time using any means;

(iii) annealing the electrostatic charged primers to the denatured nucleic acid, wherein the primers are extended by action of a polymerase and the nucleic acid is amplified; and (iv) applying an electric field for denaturing the amplified nucleic acid.

The chemical denaturation used in the context of the present invention comprises contacting the nucleic acid with NaOH at a concentration of from about 0.1 M to about 0.25 M. Alternatively, the non-thermal denaturation means used comprises applying an electric field for denaturing the amplified nucleic acid, which is a result of the electrostatic beads attached to the probes, which upon extension become amplicons, being attracted to opposite electrodes that straddle the reaction chamber and establish the electric field that mediates the electrostatic denaturation.

The present device preferably is employed in the context of conducting nucleic acid amplifications accomplished via polymerase chain reaction (PCR), ligase chain reaction (LCR), strand displacement amplification (SDA), or nucleic acid sequence-based amplification (NASBA). More preferred, the nucleic acid amplification is accomplished via PCR or LCR, comprising the following steps:

A. combining target nucleic acid and primers in a suitable buffer in the reaction chamber;

B. denaturing the target nucleic acid and primers in the first cycle by chemical means, and then in subsequent cycles by chemical or electrostatic means;

C. neutralizing or removing the chemical means in or from the reaction chamber, or removing the electric field of the electrostatic means;

D. annealing the denatured target nucleic acid in the presence of the primers; and E. contacting the annealed target nucleic acid-primers combination with a DNA polymerase or ligase.

Of course, steps (B) through (E) are preferably repeated, resulting in increased amplification. Unlike other PCR and LCR protocols, this protocol keeps the temperature constant within about two degrees centigrade, preferably between about 20° C. and about 75° C.

The device incorporates the chemical means of denaturation, which comprises contacting the nucleic acid with a base, preferably with NaOH at a concentration of from about 0.1 M to about 0.25 M. The device in addition incorporates the non-thermal electrostatic means of denaturation, comprising applying an electric field for denaturing the amplified nucleic acid.

In another aspect, the present invention relates to the method of nucleic acid amplification itself, comprising denaturing the nucleic acid by electrostatic means. The electrostatic means comprises:

(A) providing primers that are respectively complementary to the W and C strands of the nucleic acid, and have attached thereto electrostatic microparticles of positive or negative charge, wherein the primers complementary to the W strand all have the same charge and the primers complementary to the C strand all have the opposite charge;

(B) denaturing the nucleic acid for a first cycle using a non-electrostatic means;

(C) annealing the electrostatic charged primers to the denatured nucleic acid, wherein the primers are extended by action of a polymerase and the nucleic acid is amplified; and (D) applying an electric field for denaturing the amplified nucleic acid in succeeding cycles.

The inventive nucleic acid amplification method comprising electrostatic means further comprises (1) combining target nucleic acid and primers;

(2) denaturing the target nucleic acid and primers by a non-electrostatic means in a first cycle, and by the electrostatic means in succeeding cycles, wherein in the first cycle if chemical means are used to denature the target nucleic acid, then the chemical means is neutralized or removed in or from the environs of the target nucleic acid and primers;

(3) renaturing the denatured target nucleic acid in the presence of the denatured primers, thereby forming a target-primer complex;

(4) contacting the target-primer complex with a nucleotide polymerase; and (5) repeating steps (2) through (4);

wherein the temperature remains constant within about two degrees centigrade.

Further, the electrostatic means of denaturation comprises:

(A) providing primers that are respectively complementary to the W and C strands of the nucleic acid, and have attached thereto electrostatic microparticles of positive or negative charge, wherein the primers complementary to the W strand all have the same charge and the primers complementary to the C strand all have the opposite charge;

(B) denaturing the nucleic acid for a first cycle using any means;

(C) annealing the electrostatic charged primers to the denatured nucleic acid, wherein the primers are extended by action of a polymerase and the nucleic acid is amplified; and (D) applying an electric field for denaturing the amplified nucleic acid in succeeding cycles.

DEFINITIONS

The following terms shall have the meaning set forth below:

Cassette a disposable device for conducting reactions therein having a cassette body, one or more upper membranes and one or more lower membranes which together define one or more supply chambers, one or more reaction chambers and fluid exchange channels connecting the supply chambers to reaction chambers.

Connection or Communication (Between Fluid Chambers, Inlets or Detection Channels)

two fluid chambers, inlets or detection channels are "connected" or have a "route of connection" or communicate therebetween if there is one or more fluid exchange channels joining the two such that fluid can move from one to the other.

Fluid Chamber the term "fluid chamber" encompasses reaction, supply, waste metering and sample storage chambers, and other fluid containing chambers. In those embodiments where contents of the chambers can be pumped out using a foot-pad having a shape that conforms to a covering film that is inverted to match the shape of the bottom of the chamber, the chamber can be closed by maintaining the foot-pad pressed against the inverted covering film.

Microparticle a microparticle can have any shape, which is preferably spherical. Preferably, it has a diameter of less than 1 mm, and more preferably, less than 500 microns. In certain preferred embodiments, the microparticles have a diameter from about 0.5 micron to about 25 microns, and more preferably from about 1 micron to about 5 microns, and even more preferably, about 2 microns to about 4 microns. Microparticles are comprised of any suitable material, the choice of material being guided by its characteristics, which preferably include minimal non-specific adsorptive characteristics, such as that of polystyrene. In other embodiments, the microparticles are comprised of, for example, plastic, glass, cellulose, a cellulose derivative, nylon, polytetrafluoroethylene ("TEFLON"), ceramic and the like. A paramagnetic bead can be comprised of, for example, iron dispersed in a polystyrene matrix, and can be obtained, for example, from Dynal (Oslo, Norway).

Reaction Chamber a fluid chamber for locating reactants undergoing or to undergo a reaction, comprised of any suitable material, i.e., a material that exhibits minimal non-specific adsorptivity or is treated to exhibit minimal non-specific adsorptivity, which material can be, for example, glass, plastic, nylon, ceramic, or combinations thereof, and is connected to at least two fluid exchange channels for passaging material in and out of the reaction chamber.

Reaction Flow-Away a series of two or more serially connected fluid chambers through which fluids can move.

Serially Connected two or more fluid chambers are serially connected if there are fluid exchange channels by which fluid from a first of the serially connected chambers can pass to a second of the serially connected chambers, and from there to a third of the serially connected chambers, and so on until the fluid passes to the last of the serially connected chambers.

Target Nucleic Acid Segment a segment of nucleic acid that is sought to be identified or measured in a sample, such as a sequence intended, if present, to be amplified in a nucleic acid amplification reaction such as a PCR reaction, strand displacement assay or ligase chain reaction; the target segment is typically part of a much larger nucleic acid molecule found in the sample.

DETAILED DESCRIPTION

The present invention relates to an isothermal method of nucleic acid amplification. By removing the need to incorporate heat cycling in an amplification reaction, the cost of the method is substantially reduced, both for the avoidance of requiring a thermal cycler component of any amplification equipment, and for the ability to use polymerases well known in the art that are inexpensive to purchase or prepare, such as, for example, *E. coli* DNA polymerase I, Klenow fragment derived therefrom, T7 DNA polymerase, or RNA polymerase or a fragment thereof having polymerase activity derived from *E. coli*, for example. Moreover, this method is automatable, and may be used in the context of the microfluidics device disclosed in a related U.S. patent application Ser. No. 60/010,513, filed Jan. 24, 1996, which is incorporated herein by reference. As set forth hereinbelow, the present invention also relates to a device that employs the aforementioned amplification method.

The amplification method of the present invention relates to any suitable procedure for amplifying a nucleic acid that is known in the art, but which is altered to incorporate nonthermal means for denaturing or denaturing the target nucleic acid or resultant amplification products, which of course are also nucleic acids. Such suitable procedures, standard procedures of which are noted by reference, include the following: (1) Polymerase chain reaction (PCR; see, e.g., U.S. Pat. No. 4,683,202 and *Short Protocols In Molecular Biology* (Frederick M. Ausubel et al., eds. 1992)(hereinafter, Ausubel et al.), Unit 15.1); ligase chain reaction (LCR; see, e.g., European Patent Publication 320,308 and Schachter et al., *J. Clin. Microbiol.*, 32, 2540–2543 (1994)); strand displacement amplification (SDA; see, e.g., Walker et al., *PCR Methods and Applications*, 3, 1–6 (1993)); nucleic acid sequence-based amplification (NASBA; see, e.g., van Gemen et al., *J. Virol. Methods*, 43, 177–188 (1993)); and transcription-mediated amplification (TMA; Pfyffer et al.,*J. Clin. Micro.*, 34, 834–841 (1996)).

The first two amplification procedures, the PCR and LCR methods, both relate to amplification of DNA segments, and are commonly used in methods of detection and analysis of such segments. These procedures commonly are used with thermal cyclers for generating cycling denaturing-renaturing/reaction temperatures for the reaction. The other two amplification procedures, the SDA and NASBA, also can be used to amplify a DNA segment, but provide RNA amplification products. Typically, these procedures require at least an initial high temperature incubation to provide for the denaturing of the target DNA upon or prior to the adding of primer, after which the reactions are conducted isothermally at a lesser temperature. For example, the NASBA procedure referenced above includes an initial incubation at 75° C. followed by incubations at 41° C. Similarly, the SDA procedure, also referenced above, includes an initial incubation at 95° C. followed by incubations at 37° C. A preferred embodiment of the present method obviates the requirement to have any such fluctuation of temperature, making the inventive procedure more amenable to automation and to the use of relatively less expensive enzymes that need not be thermophilic.

Another embodiment of the present invention contemplates an adaptation of the aforementioned amplification methods to accommodate a fully chemical method with respect to both denaturation and ligation. In addition to the chemical denaturation more fully described below, the fully chemical embodiment of the present invention includes chemical means for ligating two abutting oligonucleotides. Such methods include the use of cyanogen bromide or carbodiimide, for example, which are used in accordance with conventional procedures. See, for example, Rubin et al., *Nucleic Acids Res.*, 23, 3547–3553 (1995); and Ng and Orgel, *Nucleic Acids Res.*, 15, 3573–3580 (1987). Additionally, with respect to transcription amplification methodologies that incorporate reverse transcriptase conversion of the RNA amplicon to its DNA complement, instead of using RNase H or heat to remove the RNA amplicons from their DNA copies, the chemical approach of contacting the reverse transcriptase product with alkali would serve to hydrolyze the RNA, and leave single-stranded DNA ready for a succeeding round of amplification. The fully chemical embodiment is particularly well-suited to the microfluidic environment because but for the microfluidic environment problems stemming from evaporation as well as inconstant volumes essentially preclude this approach in a single tube environment.

As a general rule, the present method requires that the temperature of the reactants of an amplification procedure be maintained at certain levels for the effective and efficient use of certain enzymes used in the amplification procedure; in some embodiments, the method performs effectively at ambient room temperature, such as between about 20° C. and about 30° C. Other embodiments require the temperature of the reactants to be higher, say up to about 75° C. However, in contrast to the methods described above, the method set forth herein is fully effective under isothermic conditions, albeit one could operate a method of the present invention using alternating temperatures, or an initial temperature at one level followed by incubation for the remainder of the procedure at a second level.

In one embodiment of the present invention, an electrostatic means is employed to denature the resultant amplicons of a nucleic acid amplification procedure. Using this embodiment, nucleic acid amplification is accomplished by first combining target nucleic acid and primers and then denaturing the target nucleic acid and primers by a non-electrostatic means in a first cycle, and by an electrostatic means in succeeding cycles. In the first, cycle if chemical means are used to denature the target nucleic acid, then the chemical means is neutralized or removed in or from the environs of the target nucleic acid and primers, thus renaturing the denatured target nucleic acid in the presence of the denatured primers, and forming a target-primer complex. As will be further described below, the microfluidics environment is particularly preferred to mediate the initial chemical-based denaturation, which preferably is effected by subjecting the target nucleic acid to about 0.1 M to about 0.25 M base, such as NaOH, followed by neutralization of the chemical means denaturation. Preferably, the target nucleic acid is attached to a solid surface, such as a microparticle having specific affinity for nucleic acid, more preferably a microbead having an average diameter of between about $0.05\mu$ to about $10\mu$. One such bead is a Dynabead, vended by Dynal Corporation. Others include Estapor microparticles (Bangs Laboratory, Carmel, Ind.), for example. If the microparticle is paramagnetic, for example, the microparticle can be caused to be locked in a position by a magnetic field, and the chemical denaturant, followed by neutralization fluid, followed by primers and amplification reaction mixture specific for the chosen amplification reaction can be caused to flow past and among the target nucleic acid in sequence using the microfluidic environment set forth in the aforementioned U.S. patent application Ser. No. 60/010,513. The target-primer complex is next contacted with a suitable nucleotide polymerase, wherein a nucleotide polymerase is suitable with respect to whether the template is RNA or DNA, the polymerase synthesizes RNA or DNA, and, in accordance thereto, whether ribo- or deoxyribonucleotide triphosphates are in the reaction mixture, all of which are selected in accordance with procedures set forth in Ausubel et al. and Sambrook et al., *Molecular Cloning, A Laboratory Manual* (2d ed., 11989). The temperature of the reactants in this method preferably remains constant within about two degrees centigrade, wherein the temperature is between about 20° C. and 75° C.

The denaturing or denaturing of a target nucleic acid or amplification products which are nucleic acids (termed "amplicons") as well is preferably accomplished by non-thermal means. Such means can be chemical means or electrostatic means, for example. In a preferred embodiment, the means is electrostatic in nature, although as described, chemical or other means is used for the first cycle of the electrostatic-based amplification method, wherein the target nucleic acid is denatured, in order to hybridize with primers, for example. The temperature at which the inventive method is used preferably remains constant within about two degrees centigrade, wherein the temperature is between about 20° C. and about 75° C. The target nucleic acid that is amplified in the present method can be DNA or RNA, although it is more common to start with a target nucleic acid composed of DNA.

For the present method, the electrostatic means comprises (A) providing primers that are respectively complementary to the two strands of the target DNA, which according to convention are arbitrarily labeled the W and C strands of the nucleic acid, and have attached thereto suitable electrostatic microparticles of positive or negative charge, wherein the primers complementary to the W strand all have the same charge and the primers complementary to the C strand all have the opposite charge. The primers, which are used in the context of any of the embodiments discussed herein for this invention, are of any suitable length, suitability of length being a function of capability to hybridize to a unique position on target and amplicon nucleic acid, and are preferably from about 20 nucleotides to about 1000 nucleotides; more preferably, from about 20 nucleotides to about 500 nucleotides; yet more preferably, from about 20 nucleotides to about 200 nucleotides. Primers can be of a defined sequence of nucleotides, where such information is known, or can be a collection of redundant primers designed by knowledge of the amino acid sequence of a protein, and application of the genetic code using methods well-known in the art, the encoding gene or mRNA for which is sought using the amplification method of the present invention. Suitable electrostatic microparticles are comprised of any suitable material, wherein a suitable material is capable of holding an electric charge, such as plastic, metal, glass, and the like. Such microparticles can be of any suitable shape, including rods and beads, for example, and have a diameter of from about $0.5\mu$ to about $25\mu$, more preferably, from about $1\mu$ to about $10\mu$, yet more preferably from about $2\mu$ to about $4\mu$. Suitable electrostatic microparticles are any matter that has a positive or negative charge under reaction conditions. Preferred such electrostatic microparticles include those with a central conductive core covered by a layer of an insulator material or protein molecules that are charged positively or negatively at the reaction conditions being used. The microparticles are attached to the primers using any suitable means, including attachment via Protein Nucleic Acids (PNA; Perseptive Biosystems, Framingham, Mass.), biotin, avidin, streptavidin, an antigen, an antibody that recognizes the antigen, an amine, or hydrazine, among others. Preferred attachment means include biotin and streptavidin.

The electrostatic means of the present invention further comprises denaturing the nucleic acid for a first cycle using any suitable means. Presuming that the target nucleic acid is DNA, the W and C strands must be separated, which can be accomplished by application of heat, enzymes, or chemicals. Preferably, a nonthermal means is used, such as by application of an enzyme from the class of enzymes known as helicases or the bacterial enzyme RecA, which has helicase activity, which in the presence of riboATP is known to denature DNA. The reaction conditions suitable for separating the strands of nucleic acids with helicases are described by Kuhn et al., in *Cold Spring Harbor Symposia on Quantitative Biology, Vol. XLIII,* 63–67 (1978); techniques for using RecA are reviewed by Radding, *Ann. Rev. Genetics,* 16, 405–437 (1982). An alternative and preferred means entails the contacting of the target nucleic acid with a suitable base such that the W and C strands of the nucleic acid separate. Suitable bases include NaOH, which preferably is used at a concentration of about 0.1 M to about 0.3

M, more preferably from about 0.1 M to about 0.2 M. Other bases can be used for chemical denaturation, as is known in the art; one of ordinary skill in the art can determine empirically what a suitable concentration is using standard techniques for any given base, which concentration can be further adjusted for any given length range of nucleic acid that is used. One of ordinary skill will appreciate that the electrostatic means could be entirely supplanted by the chemical means just described for denaturing a nucleic acid in the context of one of the aforementioned amplification procedures, which also would provide an isothermic method for nucleic acid amplification, which approach is further discussed below.

The electrostatic means of the present invention further comprises (C) annealing the electrostatic charged primers to the denatured nucleic acid, wherein the primers are extended by action of a suitable polymerase, chosen as per the earlier discussion herein, and the nucleic acid is amplified. The suitable polymerase can be a DNA-directed RNA or DNA polymerase or an RNA-directed reverse transcriptase or suitable fragments thereof. Such suitable polymerases and fragments thereof include, but are not limited to, *E. coli* DNA polymerase I, Taq DNA polymerase, Klenow fragment, T7 DNA polymerase, and DNA polymerase derived from *E. coli*. Preferred polymerases or fragments thereof include Klenow fragment.

The electrostatic means also comprises (D) applying a suitable electric field for denaturing the amplified nucleic acid in succeeding cycles. The suitable electric field preferably is formed by the placement of opposing electrodes on two sides of a chamber or vessel, in which the amplification reactants are situated, which electrodes are attached to a suitable source of electrical power, such as a suitable power supply, and a suitable voltage is applied to the electrodes. Upon application of the voltage to the electrodes, the W strands migrate toward one electrode and the C strands migrate to the other electrode, thereby denaturing the nucleic acid contained in the chamber or vessel.

The present invention also relates to a device in which the aforementioned isothermic method of nucleic acid amplification is employed. In particular, such a device comprises a fluid chamber, which is a generic term that describes chambers designed for storage of fluid reagents or reactants, i.e., a supply chamber, for locating reactants undergoing a reaction, i.e., a reaction chamber, for measuring a volume of a fluid, i.e., a metering chamber, and more. More particularly, the inventive device includes a reaction chamber wherein suitable non-thermal means are employed for denaturing nucleic acid in the reaction chamber. The reaction chamber is comprised of any suitable material, wherein a suitable material is selected for its ability to be molded, heated, minimize adsorption of macromolecules, and other parameters. Suitable materials include, for example, glass, plastic, ceramic, or combinations thereof. Importantly, a reaction chamber used in the context of the present invention is connected to at least two fluid exchange channels for passaging material in and out of the reaction chamber, which is particularly important for employing chemical means of denaturation in the amplification procedure. The reaction chamber preferably remains at a constant temperature of within about two degrees centigrade, wherein the temperature is between about 20° C. and 75° C.

As set forth in greater detail hereinabove, the non-thermal means for nucleic acid denaturation used in the context of the present device comprises:

(A) using suitable chemical denaturation, comprising:
  (i) contacting the nucleic acid with a suitable base followed by neutralization of the base; or (B) using suitable electrostatic denaturation, comprising:
  (i) providing primers that are respectively complementary to the W and C strands of the nucleic acid, and have attached thereto suitable electrostatic microparticles of positive or negative charge, wherein the primers complementary to the W strand all have the same charge and the primers complementary to the C strand all have the opposite charge;
  (ii) denaturing the nucleic acid a first time using any suitable means, preferably using chemical means;
  (iii) annealing the electrostatic charged primers to the denatured nucleic acid, wherein the primers are extended by action of a suitable polymerase and the nucleic acid is amplified; and
  (iv) applying a suitable electric field causing the W and C strands of nucleic acid to migrate to opposite electrodes, thereby denaturing the amplified nucleic acid.

As noted above, the device of the present invention can be employed to effect nucleic acid amplification via polymerase chain reaction (PCR), ligase chain reaction (LCR), strand displacement amplification (SDA), or nucleic acid sequence-based amplification (NASBA), transcription-mediated amplification (TMA), or other nucleic acid amplification systems. Preferably, the device is used to effect nucleic acid amplification accomplished via PCR or LCR, comprising the following steps:

1. combining target nucleic acid and primers in a suitable buffer in the aforementioned reaction chamber;
2. denaturing the target nucleic acid and primers in the first cycle by a suitable chemical means, and then in subsequent cycles by suitable chemical or electrostatic means;
3. neutralizing or removing the chemical means in or from the reaction chamber, or removing the electric field of the electrostatic means;
4. annealing the denatured target nucleic acid in the presence of the primers; and
5. contacting the annealed target nucleic acid-primers combination with a suitable DNA polymerase or ligase. The inventive device can be further employed to increase the effective amplification of the process by repeating steps 2 through 5. The temperature of the reaction chamber, and preferably of the fluids passaged into the reaction chamber, preferably remains constant within about two degrees centigrade, wherein the temperature is between about 20° C. and about 75° C. The chemical or electrostatic means used for denaturing the nucleic acid in the present device is as discussed above with respect to the method of isothermal amplification.

The device of the present invention further comprises:

1. a cassette suitable for conducting nucleic acid amplification therein formed of a body, at least one upper film and at least one lower film, wherein the upper and lower films are formed of a flexible material;
2. at least one reaction flow-way in the cassette, wherein the reaction flow-way comprises two or more fluid chambers that comprise a first supply chamber and a first reaction chamber, and wherein the fluid chambers are serially connected by first fluid exchange channels;
3. one or more valves for controlling the flow of fluids through a first fluid exchange channel;
4. one or more pumps for moving fluids into and out of the fluid chambers; and 5. a first inlet port on the cassette connected to a first supply chamber in each reaction flow-way by a second fluid exchange channel. Further details of the cassette are set forth in the aforementioned U.S. patent Ser. No. 60/010,513; suffice to say here, that this cassette provides the environment of a microfluidic approach to conducting multiple amplification reactions in parallel or different target nucleic acids or the same target nucleic acid using different primers, with or without positive or negative controls that contain target nucleic acid and probes known to effectively result in amplicons, or not, respectively. Discrete, microliter volumes of reactants and denaturants, such as NaOH, and neutralizer, such as HCl, are caused to flow to, about, and past the target nucleic acid and amplicons, which are held locked in place on the aforementioned paramagnetic microparticles in the reaction chamber by the magnetic field produced by the device. Accordingly, the device using only a chemical denaturant has the advantage of not requiring the establishment of an electric field to induce denaturation. Conversely, the electrostatic approach has the advantage of requiring fluids to pass to, about, and by the amplicons only in the first cycle when the target nucleic acid must be denatured, after which cycling of the amplification reaction is effected by periodic establishment of an electric field, which design should exhibit increased efficiency in retention of amplicons.

The following examples further illustrate the present invention but, of course, should not be construed as in any way limiting its scope.

EXAMPLE 1

This example illustrates chemical denaturation of target nucleic acid.

A representative target nucleic acid, namely *E. coli* genomic DNA, was purchased from Sigma Chemical Company (Catalog #D-0421). Approximately 0.5 $\mu$g of the *E. coli* DNA was subjected to different pH and temperature conditions for denaturation, using NaOH at 0.1 M, 0.25 M, and 0.5 M, either at room temperature (above 25° C.) or 37° C. Denaturation was detected by observing decreased mobility of the base-treated *E. coli* DNA on a 0.7% agarose gel. Mobility of denatured genomic DNA will decrease relative to native genomic DNA due to the secondary structures resulting from the base-treatment. Retarded mobility was observed, thus confirming the base denaturation, which occurred with all concentrations and temperatures tested. However, the sample treated with 0.1 M NaOH at room temperature resulted in the most intense bands in the gel, which is consistent with that treatment providing the most effective denaturation.

Accordingly, the most effective concentration of the NaOH used for denaturing genomic DNA was 0.1 M, at room temperature.

EXAMPLE 2

This example illustrates chemical denaturation of an amplicon.

A bacteriophage lambda target nucleic acid was used to generate 500 base pair amplicons using a standard polymerase chain reaction, as set forth in Ausubel, et al. Approximately 0.5 $\mu$g of the 500 base pair amplicon was subjected to different conditions for denaturation, i.e., subjecting the amplicons to 0.01 M, 0.05 M, 0.1 M, 0.25 M, and 0.5 M NaOH for 10 minutes at room temperature (about 25° C.). Denaturation was detected by observing increases in the electrophoretic mobility of each treated sample or a 1.5% agarose gel. Denatured amplicons, being dramatically smaller than generic DNA and having little or no prospect of developing higher ordered structures upon denaturation, migrate faster in an electrophoretic field after denaturation. From the electrophoresis results, 0.01 M and 0.05 M did not appear to affect the amplicons relative to untreated controls, 0.1 M and 0.25 M provided similar results, and the bands on the electrophoretics gel indicated less efficient denaturation at the higher NaOH concentration of 0.5 M. Accordingly, the result indicates that the most effective concentration of the NaOH used for converting the lambda derived amplicon into a denatured form was 0.1 M.

EXAMPLE 3

This example illustrates chemical denaturation as used in an amplification procedure of the present invention.

Biotinylated primers corresponding to the bacteriophage lambda genome were synthesized (Operon Technologies, Inc., Alameda, Calif.). 20 pmoles of each of the two biotinylated primers were complexed with magnetic microparticles coated with streptavidin (Dynal, # 112.05) by the method of a handbook published by Dynal Corporation, named Biomagnetic Techniques in Molecular Biology (1995), pp. 9–27. 0.5 ng of the target DNA isolated from bacteriophage lambda was denatured by incubating in 0.1 M NaOH at room temperature for 1 minute, followed by neutralization by adding any equal volume of 0.1 M HCl. Isothermal amplification was performed at 68° C. for 2 minutes by adding the above complexed primers and denatured target DNA to amplification reaction mix for PCR. (Ausubel et al.). Denaturation of amplicon at each cycle was performed by separating the magnetic microparticles complexed to the extended primers (i.e., the amplicon), removing the amplification reaction mixture, washing the complexed microparticles with PCR buffer, and adding NaOH to a final concentration of 0.1 M. After 30 seconds at room temperature, the denatured amplicon was recovered by separating the paramagnetic microparticles with a magnetic field, aspirating NaOH and washing three times with PCR buffer. A second round of amplification was initiated by the addition of amplification reaction mix and incubation at 68° C. for 1 minute. The resulting amplicon was subjected to denaturation as above. 20 cycles of amplification were performed. One tenth of the resulting amplified product was then added to a fresh amplification tube and subjected to standard PCR. The PCR product was analyzed on 1.5% agarose gel, which resulted in a visualized discrete band. Accordingly, PCR conducted using chemical instead of heat-based denaturation was shown to work.

EXAMPLE 4

This example illustrates neutralization requirements after chemical denaturation in accordance with the present invention.

A test was set up to determine the tolerance for neutralization pipetting efficiency required for polymerase-based amplification where the target or amplicon nucleic acid is denatured using NaOH. Varying volumes of 0.1 M HCl was added to tubes containing a target DNA that was alkaline denatured in 10 $\mu$l of 0.1 M NaOH, and then used in an otherwise standard PCR system, i.e., the initial heat-denaturing step of the cycle was omitted. The results were as follows:

| Volume of 0.1 M HCl | Amplicon Observed |
|---|---|
| 12 µl | + |
| 10 µl | + |
| 8 µl | − |

As seen in the chart above, the system is very sensitive to the amount of acid actually delivered to neutralize the base denaturation. Accordingly, the device of the present invention can not tolerate short volumes of HCl delivery.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

What is claimed is:

1. An amplification device for target nucleic acids comprising a reaction chamber and at least one supply chamber, wherein amplicons complementary to a target nucleic acid segment of the target nucleic acid are generated in a reaction chamber within the device and form duplex amplicons between complementary amplicons, and wherein denaturation of the duplex amplicons is effected in the reaction chamber by a chemical denaturant or an electrostatic process wherein the device further comprises:

an electric field generating device effective to create a field at a reaction chamber of the device such that the strands of amplicons in that chamber separate, wherein the amplicons are each formed from first primer and a second primer, where the first primers have one charge and the second primers have the opposite charge.

2. The device of claim 1, wherein the reaction chamber remains at a constant temperature within about two degrees centigrade.

3. The device of claim 1, wherein the temperature is between about 20° C. and 75° C.

4. The device of claim 1, wherein nucleic acid amplification is accomplished via polymerase chain reaction (PCR), ligase chain reaction (LCR), strand displacement amplification (SDA), nucleic acid sequence-based amplification (NASBA), or transcription-mediated amplification (TMA).

5. A method for amplification of a target nucleic acid, which target nucleic acid comprises a target nucleic acid segment, comprising, in a first cycle, the steps of:

(A) providing one or more pairs of primers for creating extended primers, (B) denaturing the target nucleic acid by chemical means, (C) annealing the primers to the target nucleic acid to form a target-primer complex, (D) contacting the target-primer complex with polymerase to extend the primers of the target-primer complex, and (E) denaturing the target-primer complex of (D) by non-thermal means.

6. The method of claim 5, further comprising, in a second cycle, the steps of:

(F) annealing the extended primers of step (E) with the primers which are electrostatic charged primers, wherein one member of each pair of primers is positively charged and the other member is negatively charged to form a first extended primer-primer complex;

(G) contacting the first extended primer-primer complex of step (F) with polymerase to extend the primers and form second extended primers, (H) applying an electric field to denature the first amplicon-primer complex of step (G), (I) annealing the second extended primers of step (H) with electrostatic charged primers to form a second amplicon-primer complex, (J) contacting the second extended primer-primer complex with polymerase to extend the electrostatic charged primer, and (K) applying an electric field to denature the second extended primer-primer complex of step (J).

7. The method of claim 6, wherein amplification occurs at a temperature that remains constant within about two degrees centigrade.

8. A microfluidic device for amplifying a nucleic acid, comprising a cassette comprised of at least one reaction flow-way having at least one reaction chamber connected to at least one supply chamber by a first fluid exchange channel, an electric field generating device effective to create a field at a reaction chamber of the device such that the strands of amplicons in that chamber separate, wherein the amplicons are each formed from first primer and a second primer, where the first primers have one charge and the second primers have the opposite charge.

9. The microfluidic device of claim 8, wherein the nucleic acid or amplicon is denatured using a chemical denaturant, wherein the chemical denaturant is a base.

10. The microfluidic device of claim 9, wherein the nucleic acid or amplicon is denatured in the reaction chamber by base delivered into the reaction chamber or renatured in the reaction chamber by acid delivered into the reaction chamber via the first fluid exchange channel.

11. The microfluidic device of claim 8, further comprising one or more valves for controlling the flow of fluids through the first fluid exchange channel.

12. The microfluidic device of claim 11, further comprising one or more pumps for moving fluids into and out of the reaction chamber or the supply chamber.

13. The microfluidic device of claim 12, further comprising an inlet port on the cassette which inlet port is connected to the supply chamber in the reaction flow-way by a second fluid exchange channel.

14. The microfluidic device of claim 13, wherein the target nucleic acid and amplicons are held in place in the reaction chamber such that the chemical denaturant or a neutralizer thereof flow to, about and past the nucleic acid and amplicons.

15. The microfluidic device of claim 14, wherein the nucleic acid and amplicons are held in place in the reaction chamber by attachment to a surface.

16. The microfluidic device of claim 15, wherein the surface is a paramagnetic microparticle and the microfluidic device further comprises a magnet that imparts a magnetic field within the reaction chamber.

17. The method of claim 6, further comprising repeating steps (I) through (K).

18. The method of claim 5 further comprising, in a second cycle, (F') annealing the first amplicons of step (E) with primers to form a first amplicon-primer complex, (G') contacting the first amplicon-primer complex with polymerase to extend the primers, (H') denaturing the first amplicon-primer complex of step (G') using a chemical denaturant to provide second amplicons, (I') annealing the second amplicons of step (H') with primers to provide a second amplicon-primer complex, (J') contacting the second amplicon-primer complex with polymerase to extend the primers, and (K') denaturing the second amplicon-primer complex of (J') using a chemical denaturant.

19. The method of claim 18 wherein the chemical denaturant is a base.

20. The method of claim 19 wherein the base comprises NaOH at a concentration of from about 0.1M to about 0.25M.

* * * * *